(12) United States Patent
Bhan et al.

(10) Patent No.: US 8,021,840 B2
(45) Date of Patent: Sep. 20, 2011

(54) DIAGNOSTIC MARKER FOR INTERFERON RESPONSIVENESS IN MULTIPLE SCLEROSIS

(75) Inventors: Virender Bhan, Halifax (CA); Andrea Hebb, Eastern Passage (CA); Martin Holcik, Ottawa (CA); Robert G. Korneluk, Ottawa (CA); Craig Moore, Grand Bay-Westfield (CA); George Robertson, Halifax (CA)

(73) Assignee: Dianovix, Inc., Halifax, Nova Scotia (CA)

( * ) Notice: Subject to any disclaimer, the term of this patent is extended or adjusted under 35 U.S.C. 154(b) by 519 days.

(21) Appl. No.: 11/713,733

(22) Filed: Mar. 5, 2007

(65) Prior Publication Data
US 2007/0218493 A1 Sep. 20, 2007

Related U.S. Application Data

(60) Provisional application No. 60/778,907, filed on Mar. 6, 2006.

(51) Int. Cl.
*C12Q 1/68* (2006.01)
*G01N 33/53* (2006.01)
*C12P 19/34* (2006.01)

(52) U.S. Cl. .............................. 435/6; 435/7.1; 435/91.2

(58) Field of Classification Search ........................ None
See application file for complete search history.

(56) References Cited

U.S. PATENT DOCUMENTS
2003/0215824 A1* 11/2003 Korneluk et al. ................. 435/6

OTHER PUBLICATIONS

Ahern, The Scientist 9 (15): 20 (1995).*
Douglas W. Leaman et al, Identification of X-linked Inhibitor of Apoptosis-associated Factor-1 as an Interferon-stimulated Gene That Augments TRAIL Apo2L-Induced Apoptosis, The Journal of Biological Chemistry, Issued Aug. 9, 2002, vol. 277, No. 32, pp. 28504-28511, The American Society for Biochemistry and Molecular Biology, Inc., Bethesda, Maryland, U.S.A.
F. Gilli et al, Biological Markers of Interferon-Beta Therapy: Comparison among interferon-stimulated genes MxA, TRAIL and XAF-1, Multiple Sclerosis, Accepted Jun. 15, 2005, vol. 12, pp. 47-57, Edward Arnold Publishing Ltd., London, England, published Feb. 2006.
Stephen Cunningham et al, Pharmacogenomics of responsiveness to interferon IFN-β treatment in multiple sclerosis: A genetic screen of 100 types I interferon-inducible genes, Clinical Pharmacology & Therapeutics 2005, vol. 78, No. 6, pp. 635-646, American Society for Clinical Pharmacology and Therapeutics, Alexandria, Virginia, U.S.A.
Aksel Siva, The Spectrum of multiple sclerosis and treatment decisions, Clinical Neurology and Neurosurgery 108 (2006), pp. 333-338, Elsevier BV, Netherlands.
Van Baarsen, L.G.M. et al, A subtype of multiple sclerosis defined immune defense program, Genes and Immunity, Jul. 13, 2006, vol. 7, pp. 522-531, Nature Publishing Group, London, England.

* cited by examiner

*Primary Examiner* — James Martinell
(74) *Attorney, Agent, or Firm* — Philip Swain; Fasken Martineau DuMoulin LLP

(57) ABSTRACT

Disclosed is a method of determining interferon responsiveness in a patient suffering from multiple sclerosis. The method comprises determining an amount of a XAF-1 gene expression level in a blood sample, which is obtained from the patient undergoing interferon therapy. The amount of the XAF-1 gene expression level in the blood sample is then correlated with the responsiveness of the patient to the interferon.

37 Claims, 4 Drawing Sheets

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: Oliognucleotide chain

<400> SEQUENCE: 1
ctcggtgtgc aggaactgta aa                                              22

<210> SEQ ID NO 2
<211> LENGTH: 19
<212> TYPE: DNA
<213> ORGANISM: Artificial Sequence
<220> FEATURE:
<223> OTHER INFORMATION: Oligonucleotide chain

<400> SEQUENCE: 2
caggaaccgc aggcagtaa                                                  19

<210> SEQ ID NO 3
<211> LENGTH: 27
<212> TYPE: DNA
<213> ORGANISM: Artificial Sequence
<220> FEATURE:
<223> OTHER INFORMATION: Oligonucleotide chain
<220> FEATURE:
<221> NAME/KEY: misc_feature
<222> LOCATION: (1)..(1)
<223> OTHER INFORMATION: modified by 6-Carboxy-fluoroscein (FAM)
<220> FEATURE:
<221> NAME/KEY: misc_feature
<222> LOCATION: (27)..(27)
<223> OTHER INFORMATION: modified by 6-Carboxytetramethylrhodamine
      (TAMRA)

<400> SEQUENCE: 3
tctgccaact tcaccctcca tgaggta                                         27

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide chain
```

-continued

```
<400> SEQUENCE: 4
tgcaaacaaa tgattccaga                                              20

<210> SEQ ID NO 5
<211> LENGTH: 21
<212> TYPE: DNA
<213> ORGANISM: Artificial Sequence
<220> FEATURE:
<223> OTHER INFORMATION: Oligonucleotide chain

<400> SEQUENCE: 5
tcccgaatac gtgtcacagt g                                            21

<210> SEQ ID NO 6
<211> LENGTH: 33
<212> TYPE: DNA
<213> ORGANISM: Artificial Sequence
<220> FEATURE:
<223> OTHER INFORMATION: Oligonucleotide chain

<400> SEQUENCE: 6
tatgcctcca tatgaaacaa tgttccgccc caa                               33
```

DIAGNOSTIC MARKER FOR INTERFERON RESPONSIVENESS IN MULTIPLE SCLEROSIS

CROSS REFERENCE TO RELATED APPLICATIONS

Applicants hereby claim priority from previously filed U.S. provisional patent application No. 60/778,907, filed Mar. 6, 2006, the entire content of which are hereby incorporated by reference.

FIELD OF THE INVENTION

The present invention concerns the use of XIAP Associated Factor (XAF-1) gene expression as a diagnostic marker for interferon responsiveness in multiple sclerosis.

BACKGROUND OF THE INVENTION

Multiple sclerosis (MS) is a progressive neurological disorder characterized by an autoimmune mediated attack against the myelin sheath surrounding axons in the central nervous system (CNS) resulting in inflammation, demyelination, gliosis and ultimately axonal degeneration (Bruck and Stadelmann, 2003). The clinical course of MS is divided into four major categories (or subtypes): relapsing-remitting (RRMS), secondary-progressive (SPMS), primary progressive (PMS) and progressive relapsing (PRMS). Patients who have clinical relapses every few months or years with intervening periods of clinically stability define RRMS. RRMS is twice more common in females than males in the second or third decade of life (Noseworthy et al., 2000). In contrast to RR MS, patients with SPMS display progressive deterioration between relapses. RRMS patients may convert to SP MS over time characterized by a gradual decline in neurological function (Trojano et al., 2003). Approximately 15% of MS patients have PPMS characterized by late-onset and an unrelenting deterioration of neurological function from disease onset. Benign MS is arbitrarily defined as those RRMS patients who after more than 15 years following initial diagnosis are still mobile and show only mild deficits (Expanded Disability Status Scale [EDSS]≦4). Typically, these patients show little or no progression after their initial attack and require no therapeutic intervention; however, it is not possible to diagnose this form of MS until 5 years from MS onset (Pittock et al., 2004).

Apoptosis is an important mechanism in immune system regulation, responsible for elimination of autoreactive T cells, B cells and macrophages from the circulation and prevention of their entry into the CNS. It has been hypothesized that a failure of autoreactive T lymphocytes and B lymphocytes as well as activated macrophages to undergo apoptosis contributes to the pathogenesis of MS. Consistent with this hypothesis, expression of members of the inhibitors of apoptosis (IAP) family of anti-apoptotic proteins such as XIAP, HIAP-1, and HIAP-2 are elevated in mitogen stimulated T cells from MS patients relative to healthy or neurological control subjects (Seki et al., 1988; Semra et al., 2002; Sharief et al., 2002; Sharief and Semra, 2001; Tsukamoto et al., 1986). In a murine model of experimental autoimmune encephalomyletis XIAP knockdown using an antisense oligonucleotide decreases clinical severity (Zehntner et al., 2005). The goal of current MS therapies is to lengthen the time between relapses and thereby slow or perhaps even halt disease progression in some cases. IFN-β has been shown to lengthen the time between relapses in individuals with MS. IFN-β has been shown to reduce expression of the anti-apoptotic proteins, XIAP, HIAP-1 and HIAP-2 in mitogen stimulated T cells from MS patients suggesting that IFN-β drugs may improve the symptoms of MS by promoting the elimination of autoreactive T cells (Sharief et al., 2002).

IFN-β (Betaseron, Rebif, Avonex or Copaxone) is a very expensive therapy, which produces modest clinical benefits in MS patients. Many MS patients, however, fail to respond to IFN-β. The majority of MS patients are characterized as RRMS (85%), of which over time increasing numbers will convert to SPMS. Approximately 15% of MS patients have PPMS and do not respond to IFN-β. Currently, there are no diagnostic tests that enable a clinician to predict the likelihood of a RRMS or SPMS patient responding to IFN-β. As a result, neurologists must base a diagnosis of MS, and thereafter a decision on how to treat a patient, on neurological tests or expensive MRI scans, the latter of which being useful only in confirming the diagnosis of MS, but not to yield results that correlate with disease subtype of clinical disability. Thus there is a tremendous need for objective diagnostic tests that predict whether a patient has RRMS or SPMS on first presentation of clinical symptoms. Furthermore, given the high cost of IFN-β drugs coupled with the modest reduction in disease progression produced by these drugs, there is an urgent need for reliable, inexpensive and rapid diagnostic tests to ensure the best use of funds available for treating MS. This is especially the case in the U.S. where over 60% of MS patients are treated with these drugs, many of who experience unpleasant drug-related side effect and little clinical benefit particularly PPMS patients, but also many patients with benign MS, RRMS and SPMS.

It would therefore be highly advantageous to develop a reliable, rapid and inexpensive diagnostic test for RRMS or SPMS and IFN-β responsiveness based on specific patterns of basal gene expression in peripheral immune cells.

SUMMARY OF THE INVENTION

We have made the unexpected discovery that patients suffering from quiescent secondary progressive multiple sclerosis, and who are undergoing interferon-beta (IFN-β) treatment, have elevated XAF-1 in their T cells and peripheral blood mononuclear (PBMN) cells, but not in whole blood.

According to an embodiment of the present invention, there is provided a method of determining interferon responsiveness in a patient suffering from multiple sclerosis, the method comprising:
 a) determining an amount of a XAF-1 gene expression level in a blood sample obtained from the patient, the patient being treated with the interferon; and
 b) correlating the amount of the XAF-1 gene expression level in the blood sample with the responsiveness of the patient to the interferon.

According to another embodiment of the present invention, there is provided a method for determining a prognosis of a patient diagnosed with multiple sclerosis and undergoing IFN-β treatment, the method comprising:
 a) obtaining a blood sample from the patient; and
 b) determining whether the sample has an increased level of XAF-1 gene expression relative to that of a control subject, an increase in the level being an indication that the patient has a good prognosis and will respond to IFN-β therapy.

According to another embodiment of the present invention, there is provided a method for monitoring the progress of IFN-β therapy in a patient suffering from multiple sclerosis, the method comprising:
  a) determining an amount of a XAF-1 gene expression level in a first blood sample obtained from the patient at first time period;
  b) determining an amount of the XAF-1 gene expression level in a second blood sample obtained from the patient at a second time period; and
  b) comparing in the XAF-1 gene expression levels, an increase in the XAF-1 gene expression level at the second time period being an indication that the patient is responding to the IFN-β therapy.

According to another embodiment of the present invention, there is provided a kit for determining a patient's responsiveness to IFN-β therapy, the kit comprising:
  a) a vessel or vessels for receiving a blood sample from the patient;
  b) an agent that specifically detects XAF-1 protein or amplifies XAF-1 mRNA; and
  c) printed instructions for detecting the XAF-1 protein or the amplified XAF-1 mRNA in the sample.

According to another embodiment of the present invention, there is provided a method of differentiating between multiple sclerosis subtypes in a patient undergoing IFN-β therapy, the method comprising:
  a) determining an amount of XAF-1 gene expression level in a blood sample obtained from the patient; and
  b) correlating the amount of the XAF-1 gene expression level in the blood sample with the presence of a multiple sclerosis subtype.

According to an embodiment of the present invention, there is provided use of XAF-1 mRNA expression or XAF-1 protein expression as a biomarker for the measuring IFN-β responsiveness in a subject, an increased level of expression compared to control subjects being an indication that the patient is responsive to IFN-β.

According to an embodiment of the present invention, there is provided use of XAF-1 mRNA expression or XAF-1 protein expression as a mediator of the therapeutic effects of IFN-β.

According to an embodiment of the present invention, there is provided use of XAF-1 gene expression profiles as a surrogate biomarker for use in clinical trials for interferon-like therapies.

According to one alternative embodiment of the present invention there is provided a method for the diagnosis of a multiple sclerosis subtype in a subject, the method comprising: obtaining a peripheral blood sample from the subject, the subject being treated with IFN-β; and detecting an increased level of XAF-1 mRNA in the sample compared to the level in a healthy subject, wherein the increased level of the XAF-1 mRNA is diagnostic of the multiple sclerosis subtype in the subject.

According to another alternative embodiment of the present invention, there is provided a method for the diagnosis of a multiple sclerosis subtype in a subject, the method comprising: obtaining a peripheral blood sample from the subject, the subject being treated with IFN-β; and detecting an increased level of XAF-1 protein in the sample compared to the level in a healthy subject, wherein the increased level is diagnostic of the multiple sclerosis subtype in the subject.

According to another embodiment of the present invention, there is provided an article of manufacture comprising: a vial for receiving a peripheral blood sample from a subject suspected of having multiple sclerosis; or packaged together, a first vial for receiving the sample form the subject being treated with IFN-β and a second vial for receiving a peripheral blood sample from a healthy subject; and instructions for testing the expression of XAF-1 mRNA or XAF-1 protein in the samples and comparing the level of expression.

BRIEF DESCRIPTION OF THE DRAWINGS

Further aspects and advantages of the present invention will become better understood with reference to the description in association with the following Figures, wherein.

DETAILED DESCRIPTION OF THE INVENTION

Definitions

Figure 1:
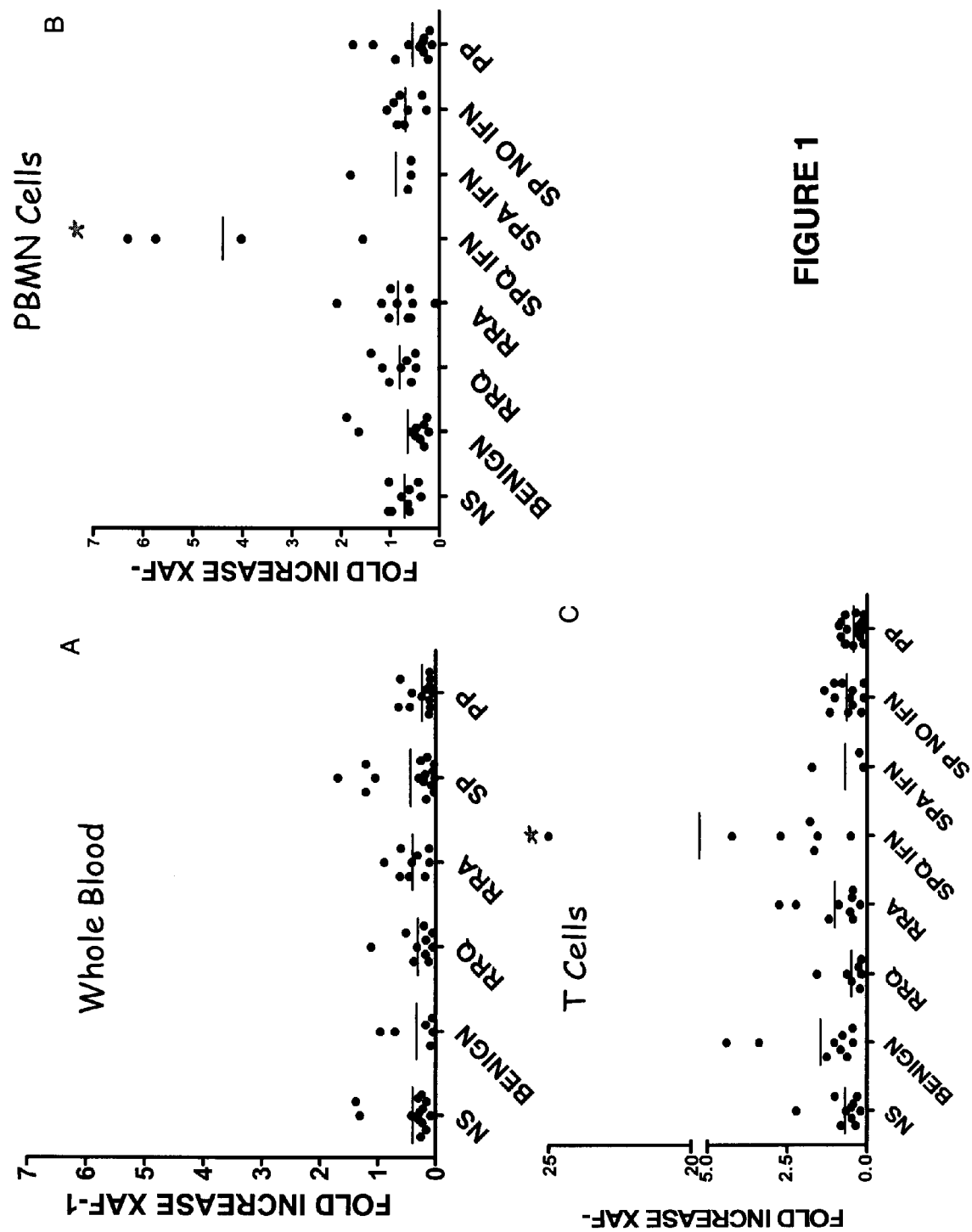
FIGS. 1A-C are graphs showing relative quantification of XAF-1 mRNA expression in RNA extracted from whole blood, PBMN cells and T cells employing qRT-PCR. These graphs depict the expression of XAF-1 mRNA relative to the expression of the endogenous control gene $\beta_2$ microglobulin ($2^{-\Delta\Delta CT}$) in normal subjects and MS patients. XAF-1 gene expression in PBMN cells was elevated only patients responsive to IFN-β treatment (SPQ IFN). All other patient groups such as SPMS patients unresponsive to this therapeutic (SPA IFN) failed to display elevated XAF-1 expression relative to the normal subjects (NS).
Q=Quiescent, MS symptoms in remission at time of blood draw. The patient has not experienced a relapse within the last year; Active=patient has experienced at least 1 relapse in the last year; Relapse=Blood is drawn during an active relapse.

Unless otherwise stated, the following terms apply:
The singular forms "a", "an" and "the" include corresponding plural references unless the context clearly dictates otherwise.

As used herein, the term "comprising" is intended to mean that the list of elements following the word "comprising" are required or mandatory but that other elements are optional and may or may not be present.

As used herein, the term "consisting of" is intended to mean including and limited to whatever follows the phrase "consisting of". Thus the phrase "consisting of" indicates that the listed elements are required or mandatory and that no other elements may be present.

As used herein the terms "apoptosis" is intended to mean the process of cell death in which a dying cell displays a set of well-characterized biochemical indicia that include cell membrane blebbing, cell soma shrinkage, chromatin condensation, and DNA laddering.

As used herein, the term "cell" is intended to mean a single-cellular organism, a cell from a multi-cellular organism or it may be a cell contained in a multi-cellular organism.

As used herein, the term "subject" or "patient" is intended to mean humans and non-human mammals such as primates, cats, dogs, swine, cattle, sheep, goats, horses, rabbits, rats, mice and the like. In one example, the subject is a human.

As used herein, the term "protein", "polypeptide" or "polypeptide fragment" is intended to mean any chain of more than two amino acids, regardless of post-translational modification, for example, glycosylation or phosphorylation, constituting all or part of a naturally occurring polypeptide or peptide, or constituting a non-naturally occurring polypeptide or peptide.

As used herein, the term "blood sample" is intended to mean whole blood taken from the periphery of the subject from which immune cells, for example, peripheral blood mononuclear (PBMN) cells; and T cells can be isolated.

As used herein, the term "XAF-1 mRNA expression" is intended to mean expression of genes which encodes XAF-1.

As used herein, the terms "XAF-1", "XAF-1 protein", or "XAF-1 polypeptide" is intended to mean a polypeptide, or fragment thereof, which has at least 30%, more typically at least 35%, and most typically 40% amino acid identity to the amino-terminal 131 amino acids of the human XAF-1 (SEQ ID NO.: 2) polypeptide. It is understood that polypeptide products from splice variants of XAF gene sequences are also included in this definition. In one example, the XAF protein is encoded by nucleic acid having a sequence which hybridizes to a nucleic acid sequences present in SEQ ID NO.: 1 under stringent conditions. The XAF polypeptide has at least three zinc finger domains. The XAF polypeptide has at least six zinc finger domains, at least five of which occur within 150 amino acids of the N-terminus. The SEQ ID NOs refer to the sequences as disclosed in U.S. Pat. Nos. 6,107,088; 6,495,339; and 6,946,544, the contents of which are hereby incorporated by reference.

As used herein, the term "XAF-1 gene" is intended to mean a gene encoding a XAF-1 protein as disclosed in U.S. Pat. Nos. 6,107,088; 6,495,339; and 6,946,544, the contents of which are hereby incorporated by reference.

As used herein, the term "biomarker" is intended to mean a detectable level of either XAF-1 mRNA or XAF-1 protein in such a pattern characterizing a specific MS subtype. In one example, the subtype is quiescent secondary progressive multiple sclerosis.

As used herein, the term "multiple sclerosis subtype" is intended to mean one or more of four categories of multiple sclerosis and includes relapsing-remitting (RRMS), secondary-progressive (SPMS), primary progressive (PPMS) and benign. The term "relapsing-remitting multiple sclerosis" can be further categorized into quiescent relapsing-remitting multiple sclerosis (RRQ) and active relapsing-remitting multiple sclerosis (RRA). The term "secondary progressive multiple sclerosis" can be further categorized into quiescent secondary progressive multiple sclerosis (SPQ) and active secondary progressive multiple sclerosis (SPA).

As used herein, the term "aggressive form of multiple sclerosis" is intended to mean RRA and SPMS.

As used herein, the term "control subjects" is intended to mean subjects who are healthy normal, or who have been diagnosed as having benign MS.

As used herein, the term interferon-beta (IFN-β) is intended to include, for example but not limited to, commercially available BETASERON™, REBIF™, or AVONEX™.

As used herein, the term "interferon-beta (IFN-β) responsiveness" or a grammatical equivalent, is intended to mean a patient having either an active (relapses; unresponsive) or quiescent (no relapses; responsive) disease course while being treated with IFN-β.

Determination of a Patient's Responsiveness to Interferon Therapy

The present invention concerns the use of XAF-1 gene expression profiles as biomarkers to evaluate the prognosis and responsiveness of patients who are suffering from multiple sclerosis and who are undergoing IFN-β therapy. We have unexpectedly discovered that patients suffering from quiescent secondary progressive multiple sclerosis and who have been treated with IFN-β have elevated XAF-1 in their T cells and peripheral blood mononuclear (PBMN) cells, but not in whole blood. The patients were qualitatively assessed as either active (2 relapses in the last 2 years) or quiescent (no relapses in last two years). In resting T cells, XAF-1 mRNA was elevated by 5 fold in quiescent patients treated with IFN-β but not in patients that are active and treated with this therapeutic. Based on these observations, we have developed a reliable, rapid and inexpensive blood test, which is predictive of a patient's responsiveness to IFN-β in MS based on induction of XAF-1 gene expression. Such an assay will not only improve the clinical management of MS and reduce related health care costs by permitting a better match of treatment to disease, but also XAF-1 expression may serve as a surrogate marker for biochemical efficacy of new MS therapeutics. Furthermore, identifying blood markers that could form the basis for diagnostics predictive of these clinical endpoints would enable better use of resources in the treatment of MS. Currently, MRI scans are useful in the diagnosis of MS but are expensive to perform and not predictive of responsiveness to IFN-β. By being able to identify those patients that are most likely to benefit from IFN-β, it will be possible to better ensure the optimal use of resources allocated for this highly expensive treatment. A diagnostic test predictive of the therapeutic response to IFN-β drugs would also facilitate treatment by providing a biochemical measure of drug efficacy that may be used to select an appropriate drug dosage. In parallel, these tests have the potential to enable significant cost savings in the context of minimizing treatments unlikely to offer therapeutic benefit and, in some cases, providing an alternative to costly MRI scans. Lastly, development of a diagnostic assay for IFN-β responsiveness would aid the future development of MS therapeutics by providing a surrogate marker for establishing clinical efficacy.

The present invention is therefore directed towards detecting XAF-1 gene expression levels isolated from the blood of a patient with secondary progressive MS and being treated with interferon-beta (IFN-β). Those patients with XAF-1 levels 3 fold higher than found in untreated MS patients are defined as deriving therapeutic benefit from IFN-β. Also, XAF-1 mRNA expression or XAF-1 protein expression may be used as a biomarker for the measuring IFN-β responsiveness in a subject, an increased level of expression compared to control subjects being an indication that the patient is responsive to IFN-β. In addition, XAF-1 mRNA expression or XAF-1 protein expression may be used as a mediator of the therapeutic effects of IFN-β. Moreover, XAF-1 gene expression profiles may be used as a surrogate biomarker for use in clinical trials for any future interferon-like therapies.

Therefore, and in accordance with an embodiment of the present invention, there is provided a method of determining interferon responsiveness in a patient suffering from multiple sclerosis, the method comprising: a) determining an amount of a XAF-1 gene expression level in a blood sample obtained from the patient, the patient being treated with the interferon; and b) correlating the amount of the XAF-1 gene expression level in the blood sample with the responsiveness of the patient to the interferon.

For example, the XAF-1 gene expression level is compared to those of control subjects in which an increase in the XAF-1 gene expression level relative to those of the control subjects indicates that the patient is responsive to the interferon therapy. The multiple sclerosis includes the subtypes: benign MS, quiescent relapsing remitting MS, active relapsing remitting MS, primary progressive MS or secondary progressive MS. In one example, the multiple sclerosis is secondary progressive MS. In specific examples, the secondary progressive MS is either quiescent secondary progressive MS or active secondary progressive MS. The control subjects are those subjects who have been previously diagnosed as having benign MS or are healthy normal subjects.

The invention provides for quantitative detection and determination of the XAF-1 gene expression levels by measuring either the levels of transcribed XAF-1 mRNA or the level of XAF-1 protein in the blood sample. One skilled in the art will recognize that many techniques are available to measure the levels of the aforesaid XAF-1 gene expression levels. The XAF-1 gene encodes XAF-1 protein. In one example, XAF-1 mRNA is measured using quantitative real time polymerase chain reaction (qRT-PCR), which is described in more detail below, whereas XAF-1 protein level is measured using an immunoassay.

Immunoassays for example include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, fluorescent immunoassays and the like. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding an antibody of interest to the cell lysate, incubating for a period of time (e.g., 1-4 hours) at 4 degrees C., adding protein A and/or protein G sepharose beads to the cell lysate, incubating for about an hour or more at 4 degrees C., washing the beads in lysis buffer and re-suspending the beads in SDS/sample buffer. The ability of the antibody to immunoprecipitate a particular antigen can be assessed by, e.g., western blot analysis. One skilled in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $.sup.32P$ or $.sup.125I$) diluted in blocking buffer, washing the membrane in wash buffer, and detecting the presence of the antigen. One skilled in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen (i.e. a XAF-1 polypeptide biomarker), coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One skilled in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

In one example, peripheral blood mononuclear (PBMN) cells and T cells are typically isolated from the blood samples of the patients and are analyzed for XAF-1 gene expression levels as is described in more detail below. The XAF-1 gene expression levels are compared to those of the control subjects, an increase in the XAF-1 gene expression level relative to those of the control subjects indicates that the patient is responsive to interferon therapy. In one example the T cells are resting T cells. In both cases, XAF-1 gene expression is elevated in the resting T cells and the PBMNs in patients suffering from quiescent secondary progressive MS, when compared to control subjects.

Determination of a Patient's Prognosis and Monitoring their Progress during IFN-β Drug Treatment One advantage of the methods of the present invention concern a clinician's ability to continue treating MS sufferers with interferon drugs, such as REBIF 22™, REBIF 44™, AVONEX™, and BETASERON™. Thus, according to an alternative aspect of the present invention, there is provided a method for determining a prognosis of a patient diagnosed with multiple sclerosis and undergoing IFN-β treatment. The method involves determining whether a blood sample taken from the patient has an increased level of XAF-1 gene expression relative to that of a control subject. An increase in the level is an indication that the patient has a good prognosis and will respond to IFN-β therapy. In one example, the blood sample is fractionated to isolate resting T cells and/or PBMNs and XAF-1 gene expression levels are then measured in the cells. The XAF-1 gene expression levels in resting T cells or PBMNs are compared to those of control subjects. Moreover, an elevated level of XAF-1 gene expression in both T cells or PBMNs indicates that the patient is suffering from quiescent secondary progressive MS and will be responsive to IFN-β therapy. Lastly, and without wishing to be bound by theory, we believe that XAF-1 is a potential mediator of the therapeutic effects of IFN-β.

For those patients for which interferon therapy is appropriate, one aspect of the invention would be a method for monitoring the progress of IFN-β therapy of a patient suffering from quiescent secondary progressive multiple sclerosis. This method comprises determining an amount of XAF-1 gene expression level in a first blood sample obtained from the patient at first time period, followed by determining an amount of the XAF-1 gene expression level in a second blood sample obtained from the patient at a second time period. The determinations may be carried out on PBMNs or resting T cells are described herein. By comparing the difference between the XAF-1 gene expression levels, an increase in the XAF-1 gene expression level at the second time period, the clinician decides that this is an indication that the patient is responding to the IFN-β therapy and an assessment can be made by the clinician as to how quickly the patient is progressing and responding to treatment. The therapy could be continued while the XAF-1 gene expression is maintained at an elevated level.

An additional advantage of the present invention is that based on the XAF-q gene expression profiles it may be possible to differentiate between quiescent and active secondary progressive MS in a patient. Thus, the invention further provides a method of differentiating between multiple sclerosis subtypes in a patient undergoing IFN-β therapy. In this case, the method comprises determining an amount of XAF-1 gene expression level in a blood sample obtained from the patient. The XAF-1 gene expression levels are then correlated with the presence of a multiple sclerosis subtype. In one example, an increased level of the XAF-1 gene expression in T cells and PBMNs isolated from the patient blood sample being an indication that the patient is suffering from quiescent secondary progressive multiple sclerosis and not active secondary progressive multiple sclerosis.

Diagnostic Kits

Generally, speaking a clinician's office may be adapted to aid quick and reliable diagnosis of a patient suspected of having one of the above mentioned subtypes of MS. Thus, according to one embodiment of the invention, there is provided a diagnostic kit for diagnosing a patient suspected of having a subtype of multiple sclerosis. The kit comprises a vessel or vessels for receiving a blood sample taken from the subject, an agent that specifically detects XAF-1 protein or amplifies XAF-1 mRNA; and printed instructions for detecting the XAF-1 protein or the amplified XAF-1 mRNA in the sample.

For example, the kits can be used to detect any one or more of the XAF-1 gene expression levels, such as XAF-1 mRNA or XAF-1 polypeptide described herein, which biomarkers are differentially present in samples of a patient and normal subjects. The kits of the invention have many applications. For example, the kits can be used to determine a patient's responsiveness to interferon-beta treatment. Also, the kits can be used to identify compounds that modulate expression of XAF-1 mRNA or protein in in vitro or in vivo animal models to determine the effects of treatment.

The XAF-1 protein can be detected using immunoassays as described above. In one example, a kit comprises (a) an antibody that specifically binds to an XAF-1 polypeptide; and (b) a detection agent. Such kits can be prepared from the materials described in U.S. Pat. Nos. 6,107,088; 6,495,339; and 6,946,544.

In the case of XAF-1 mRNA, the agent for amplifying the XAF-1 mRNA are the primers and probes selected from Table 2 below. In some instances, the kit may further comprise instructions for suitable operation parameters in the form of a label or a separate insert.

The invention also includes a diagnostic kit which includes a substantially isolated antibody specifically immunoreactive with XAF-1 polypeptide antigens, and means for detecting the binding of the polypeptide antigen to the antibody. In one example, the antibody is attached to a solid support. In a specific example, the antibody may be a monoclonal antibody. The detecting means of the kit may include a second, labeled monoclonal antibody. Alternatively, or in addition, the detecting means may include a labeled, competing antigen.

Optionally, the kit may further comprise a standard or control information so that a test sample can be compared with a control information standard to determine if the test amount of a XAF-1 biomarker detected in a sample is indicative of a quiescent relapsing remitting MS in a patient clinically diagnosed with MS and undergoing interferon-beta treatment.

Optionally, the kit can further comprise instructions for suitable operational parameters in the form of a label or a separate insert. For example, the kit may have standard instructions informing a consumer how to wash a probe after a sample is contacted on the probe. In another example, the kit may have instructions for pre-fractionating a sample to reduce complexity of XAF-1 proteins in the sample. In another example, the kit may have instructions for automating the fractionation or other processes.

The methods described above and below may also be carried out on patient blood samples, which may have been obtained and stored according to methods known to those skilled in the art of blood sample handling and storage. Thus it is within the scope of the present invention to provide a method of differentiating between multiple sclerosis subtypes in a patient undergoing interferon-beta therapy, such as quiescent relapsing remitting and active relapsing remitting in a patient blood sample. In this case, the method comprises determining an amount of an XAF-1 gene expression level in the blood sample, as described above, and then correlating the amount of the XAF-1 gene expression level in the blood sample with the presence of a multiple sclerosis subtype.

Materials and Methods

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

Unless otherwise stated, the following abbreviations are used throughout:
CNS=central nervous system;
CSF=cerebral spinal fluid;
EDSS=Expanded Disability Status Scale;
MRI=Magnetic Resonance Imaging;
MS=multiple sclerosis;
PBMN cells=peripheral blood mononuclear cells;

RR=relapsing-remitting;
RRQ=relapsing-remitting quiescent disease activity;
RRA=relapsing-remitting active disease;
RRMS=relapsing remitting Multiple Sclerosis,
SP=secondary-progressive;
SPMS=secondary-progressive Multiple Sclerosis;
PP=primary progressive;
PPMS=primary-progressive Multiple Sclerosis;
qRT-PCR=quantitative reverse transcriptase polymerase chain reaction; and
XAF-1=(X-linked inhibitor of apoptosis protein) associated factor-1.

1. XIAP-Associated Factor-1 (XAF-1) as a Prognostic Marker for Interferon-Beta (IFN-β) Responsiveness in Multiple Sclerosis The purpose of this study was to determine if XAF-1 has prognostic value for interferon-beta (IFN-β) responsiveness in relapsing-remitting (RR) and secondary-progressive (SP) MS. We have profiled mRNA and protein expression in peripheral blood mononuclear (PBMN) and subsets of peripheral T cells isolated from a cross-section of patients that have been diagnosed with RRMS or SPMS using quantitative RT-PCR methodology from MJ Research Inc. and Aegera Therapeutics Inc. and Western Blotting techniques from Aegera Therapeutics Inc., respectively. We collected and analyzed blood samples from patients with benign (n=4-5), RRMS (n=15-18), SPMS (n=12-14) and PPMS (n=5) patients for expression of XAF-1. We have also analyzed the expression of XAF-1 in (n=5) normal neurologically-healthy age matched and sex matched control subjects. Additional blood samples are also collected from normal subjects as well as patients with RRMS (n=150) and SPMS (n=150). Patients with RRMS and SPMS consist of three groups: RR and SP patients responsive to IFN-β (n=50), RR and SP patients unresponsive to IFN-β (n=50) and RR and SP patients not treated with IFN-β (n=50). Responsiveness to IFN-β treatment was defined by a patient having either an active (relapses; unresponsive) or quiescent (no relapses; responsive) disease course while treated with this therapeutic.

Forty milliliters (mL) of blood was collected, on one occasion only from each study participant. Forty mL of blood was needed for this study because T cells represent only a fraction of the total cell populations present in a blood sample and the yield of total RNA and protein from these cells are typically low. Blood was drawn in four 8 ml sodium citrate BD Ficoll gradient blood vacutainers, two 2.5 ml tube specialized for RNA extraction and one 3 ml tube for blood serum protein extraction. Each tube was labeled with a unique study identification number and a file linking this study number to the Dalhousie Multiple Sclerosis Research Unit (DMSRU) database was kept. No personally identifying information was attached to the blood sample and analysts without access to personal identifying information performed data analyses only on anonymous data files. This study design and ethical consent was reviewed and granted permission to be performed by the Ethics Review Board of the Capital District Health Association of hospitals in Halifax, Nova Scotia.

2. RNA Expression, Cell Purification, RNA Amplification and Statistical Quantification:

Highly purified T cells (2×105) were isolated from whole blood of MS patients by negative selection (StemCell Technologies, Vancouver, BC). Negative selection was chosen over positive selection in order to minimize T cell activation. In brief, 32 ml of blood was collected directly into four 8 ml CPT BD vacutainers. Four hundred microliters (μL) of RosetteSepT (Stem Cell Technologies) were added to two tubes, incubated at room temperature for 20 minutes, inverted once to mix and centrifuged at 1650-1800×g for 25 minutes in a swinging bucket centrifuge. The other 2 tubes were used for peripheral blood mononuclear (PBMN) cell isolation (RosetteSepT withheld). The plasma, PBMN cells and the enriched T cells were pipetted off into fresh tubes, and stored at −80° C. until RNA and protein extraction.

Total RNA was extracted from half of the total PBMN and T cell samples from each patient using the Qiagen RNeasy kit (Mississauga, Ontario) according to the manufacturer's instructions. All sample preparations included RNAse-free DNAse treatment. Total RNA yields were measured by UV absorbance and overall RNA quality assessed by gel electrophoresis and staining for visualization of RNA band integrity. Quantitative RT-PCR was performed to confirm changes in IAPs in different types of MS relative to normal control subjects. Aegera Therapeutics Inc. provided cDNAs, Taqman probes and Taqman primers for XAF-1 as given in the Table below:

```
FORWARD PRIMER SEQUENCE
Human XAF 1
                                      (SEQ ID NO. 1)
  5'-CTC GGT GTG CAG GAA CTG TAA A-3'

REVERSE PRIMER SEQUENCE
                                      (SEQ ID NO. 2)
  5'-CAG GAA CCG CAG GCA GTA A-3'

PROBE SEQUENCE
                                      (SEQ ID NO. 3)
  5'-(FAM)TCT GCC AAC TTC ACC CTC CAT GAG
  G(TAMRA)-3'
```

Total RNA isolated from PBMN and T cells were reverse transcribed to yield first-strand cDNA and amplified using the Taqman one-step EZ RT-PCR Core reagents kit (Applied Biosystems, Foster City, Calif., USA). A standard curve (e.g. a calibrator) was set up based on cDNA plasmid serial dilutions. Five μL from $10^6$, $10^5$, $10^4$, $10^3$, $10^2$, $10^1$ dilution series were used as templates to amplify each PCR product itself. Based on the concept that an increase in signal during the log-linear phase in each sample PCR corresponded directly to an increase in DNA, an external standard curve between initial copy numbers and crossing-point for each sample was established. The initial copy numbers of target gene in the mixture of cDNA samples was determined from this standard curve.

To detect XAF-1, we used forward and reverse primers at a concentration of 600 nmol/L and all the Taqman fluorogenic probes (200 nmol/L) as described below.

Total RNA (50 ng) isolated from whole blood, PBMN or T cells was reverse transcribed to yield first-strand cDNA and amplified using the Taqman one-step EZ RT-PCR Core reagents kit (Applied Biosystems, Foster City, Calif., USA). For detection of each IAP, forward and reverse primers were used at a concentration of 600 nmol/L and all the Taqman fluorogenic probes at a concentration of 200 nmol/l. β2 microglobulin expression was used as an endogenous control reference (Applied Biosystems, Foster City, Calif., USA). β2 microglobulin was amplified using Taqman β2 Microglobulin Control Reagents Kit (Applied Biosystems, Foster City, Calif., USA). The Taqman probe and primer sequences for the IAPs are presented in Table 2. All amplifications were done in triplicate within the same 96 well plate. Data were collected and amplification plots generated using MJ Research Inc. (USA) software. Quantification of IAP gene expression relative to β2 microglobulin was calculated according to the experimental protocol's $2^{-\Delta\Delta C_T}$ method (Livak K J, Schmittgen T D. Analysis of relative gene expression data using real-time quantitative PCR and the 2(-Delta Delta C(T)) Method. Methods 2001; 25: 402-408). Following PCR amplification, the resultant data were analyzed using software provided by MJ Research and exported into an Excel/SPSS spreadsheet for further statistical analysis. Results were expressed as Fold increase relative to a "calibrator." The calibrator sample was the RNA sample from a normal age-matched female subject.

Expression of glyceraldehyde-3-phosphate dehydrogenase (GAPDH) or beta 2 microglobulin was used as endogenous references (Applied Biosystems, Foster City, Calif., USA). All amplifications were performed in duplicate within the same 96 well plate and threshold cycle (CT) scores averaged for subsequent calculations of relative expression values. The CT scores represent the cycle number at which the fluorescence signal ($\Delta Rn$) crosses an arbitrary (user-defined) threshold. Data were extracted and amplification plots generated with MJ Research Inc. (USA) software. Quantification of XAF-1 gene expression relative to β2 microglobulin and/or GAPDH was calculated according to the protocol's 2–$\Delta\Delta CT$ method. After the PCR amplification was done the data were analyzed using the software provided by MJ Research and then the analyzed data exported into an Excel/SPSS spreadsheet for further statistical analysis. Results were expressed in Fold increase or Relative to a "calibrator." For amplicons designed and optimized according to the Applied Biosystems guidelines (amplicon size <150 bp), the efficiency is close to one. Therefore, the amount of target, normalized to an endogenous reference (i.e., GAPDH) and relative to a calibrator (i.e., normal control RNA), is given by 2–$\Delta\Delta CT$, where CT=Cycle Threshold (fractional cycle number at which the amount of amplified target reaches a fixed threshold), $\Delta$ CT=CT, X-CT, R (difference in threshold cycles for target and reference) and $\Delta\Delta CT=\Delta$ CT (target)–$\Delta CT$ (calibrator value).

Figure 2:
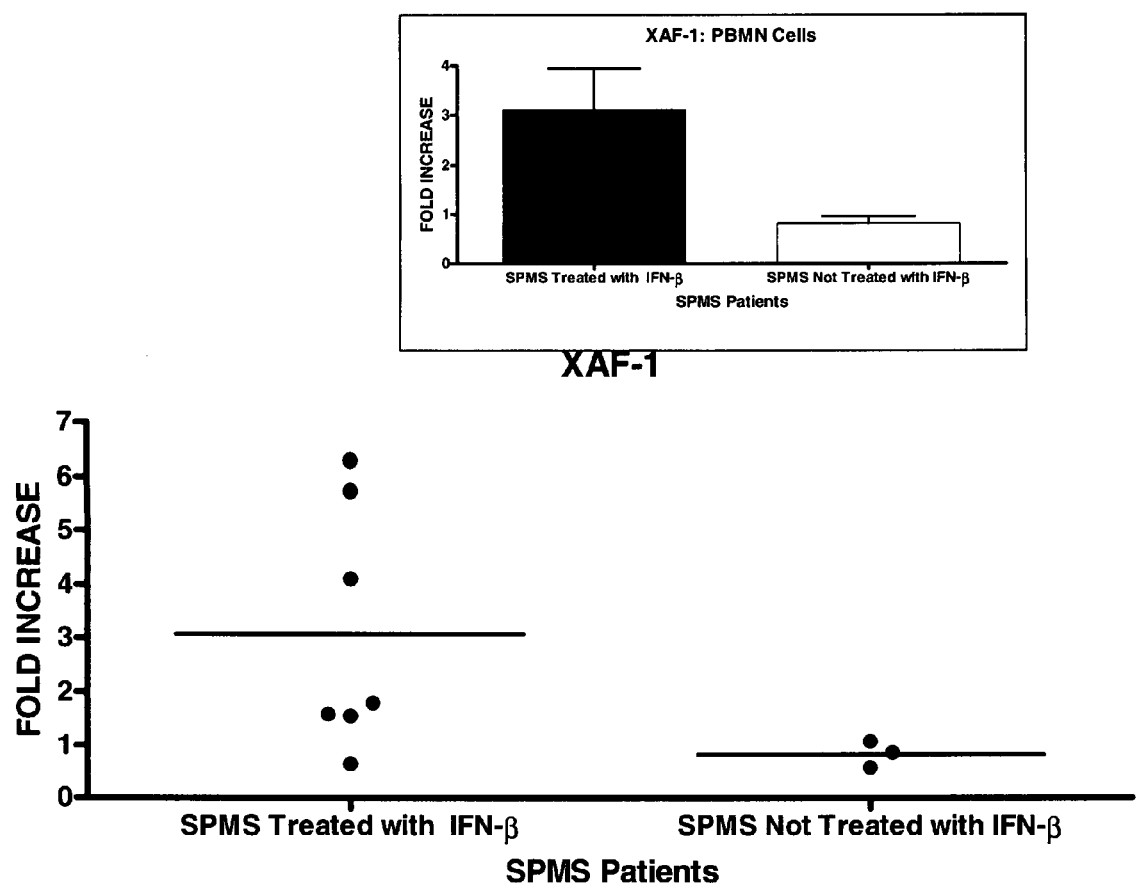
FIG. 2 is a graph showing relative quantification of XAF-1 mRNA employing qRT-PCR on RNA extracted from PBMN cells of SPMS patients. This graph shows that there was a trend for XAF-1 expression by IFN-β treatment regardless of whether the patients responded or did not respond to this therapeutic. Inset: Although SPMS patients treated with IFN-β showed trend for a general increase in XAF-1 mRNA expression from isolated PBMN cells relative to SPMS patients not treated with IFN-β, close examination of the data presented in FIG. 1 reveal that increased XAF-1 expression was restricted to those patients who derived benefit from IFN-β treatment (i.e., quiescent disease activity).

XAF-1 $\Delta\Delta C_T$ scores for each sample were subjected to a one-way analysis of variance (ANOVA), if significant post hoc comparisons of the level of XAF-1 expression among the different types of MS (RR, primary progressive, secondary progressive, benign) and normal controls were performed. Data were partitioned into disease activity and IFN-β treatment (FIGS. 1A-C) or IFN-β treatment (FIG. 2). GraphPad Prism 4 and SPSS 11.0 (SPSS, Inc., Chicago, Ill., USA) software were used for the statistical analyses. Individual group differences following significant ANOVA ($\alpha=0.05$) were determined using Tukey's HSD multiple comparisons where appropriate.

XAF-1 was identified as a novel biomarker that has high predictive value for IFN-β responsiveness in MS patients. qRT-PCR and Western Blotting studies provide complimentary results validating the potential predictive value of XAF-1.

3. Mouse Model Studies 6-8 week old female C57Bl/6 mice (Charles River, Saint-Constant, QU) were treated with recombinant mouse interferon (IFN)-beta (15000 U×3 days; Serotec, Oxford, UK) and sacrificed 2, 4, 8, and 24 hours post last injection. Control mice did not receive IFN-beta. Mice were euthanized and splenocytes were isolated. RNA was extracted using Qiagen RNA Easy® Kit (Mississauga, ON) and XAF-1 gene expression was analyzed by quantitative real-time polymerase chain reaction (qRT-PCR), using TaqMan® probes and primers (XAF-1

```
                                        (SEQ ID NO. 4)
FWD: TGCAAACAAATGATTCCAGA; XAF-1 REV:

(SEQ ID NO. 5)
TCCCGAATACGTGTCACAGTG; XAF-1 PROBE:

(SEQ ID NO. 6)
TATGCCTCCATATGAAACAATGTTCCGCCCAA.
```

The fold-change in gene expression was calculated using the –$\Delta\Delta CT$ method. A One-way ANOVA and a Tukey's post-hoc test, using triplicate replicates (n=2/group), was used to test for any statistical significance between the different groups of mice. P-value was set at <0.05.

Figure 3:
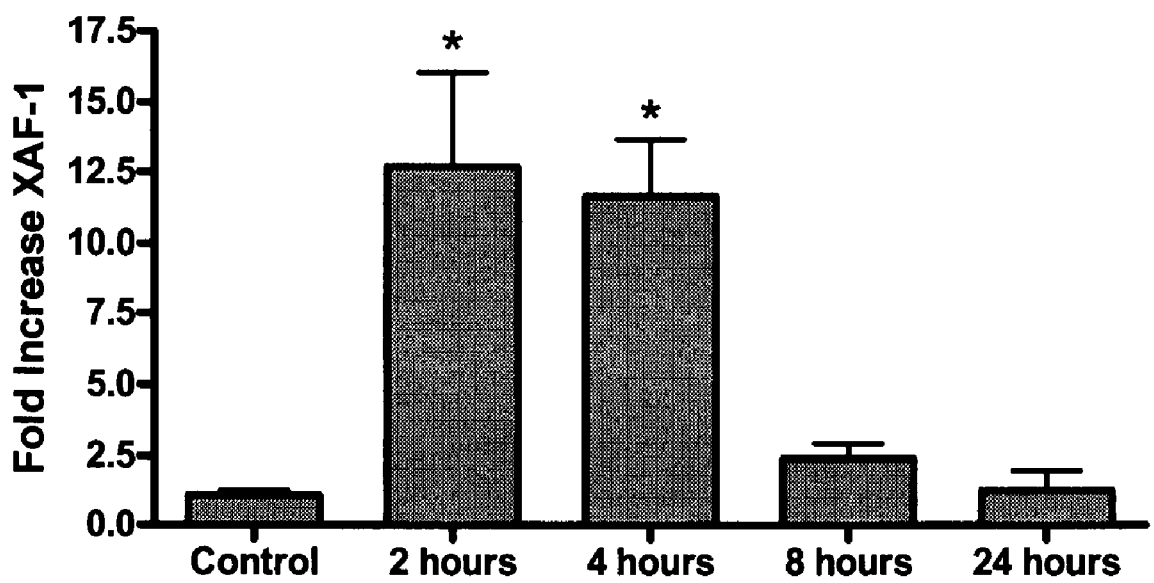
FIG. 3 is a graph illustrating that IFN-Beta (15000 U) significantly elevates XAF-1 mRNA

As shown in FIG. 3, XAF-1 expression was significantly increased 2 and 4 hours post last injection relative to mice not receiving IFN-beta and mice sacrificed 8 and 24 hours post last injection of IFN-beta.

Experimental Autoimmune Encephalomyelitis (EAE), an animal model of multiple sclerosis, was induced in 6-8 week old female C57Bl/6 mice (Charles River, Saint-Constant, QU) using 600 µg of myelin oligodendrocyte glycoprotein 35-55 (MOG35-55); (3 mg/mL) in complete Freund's adjuvant (CFA) containing 4 mg/mL *Mycobacterium tuberculosis* (Mbt) The CFA/MOG emulsion was administered subcutaneously (s.c.) at 2 injection sites on either side of the base of the tail. Mice also received 500 ng intraperitoneally (i.p.) of pertussis toxin (PTX) as an additional immune adjuvant on Days 0 & 2. The following describes the clinical scores that were assigned to each animal: Clinical Score (CS)=0→No symptoms; CS=0.5→Hooked tail; CS=1→Flaccid/Floppy tail; CS=2→Minor walking deficits; CS=2.5→Major walking deficits; CS=3→Unilateral hindlimb paralysis; CS=4→Bilateral hindlimb paralysis; CS=5→Moribund. Symptomatic EAE mice (CS=0.5-1.0~10-12 days post inoculation) were treated with recombinant mouse interferon (IFN)-beta (15000 U×3 days; Serotec, Oxford, UK) and sacrificed 2, 4, 8, and 24 hours post last injection. Control mice did not receive IFN-beta. Mice were euthanized and splenocytes were isolated. RNA was extracted using Qiagen RNA Easy® Kit (Mississauga, ON) and XAF-1 gene expression was analyzed by quantitative real-time polymerase chain reaction (qRT-PCR), using TaqMan® probes and primers (XAF-1

```
                                        (SEQ ID NO. 4)
FWD: TGCAAACAAATGATTCCAGA; XAF-1 REV:

(SEQ ID NO. 5)
TCCCGAATACGTGTCACAGTG; XAF-1 PROBE:

(SEQ ID NO. 6)
TATGCCTCCATATGAAACAATGTTCCGCCCAA.
```

The fold-change in gene expression was calculated using the –$\Delta\Delta CT$ method. A One-way ANOVA and a Tukey's post-hoc test, using triplicate replicates (n=2/group), was used to test for any statistical significance between the different groups of mice. P-value was set at <0.05.

Figure 4:
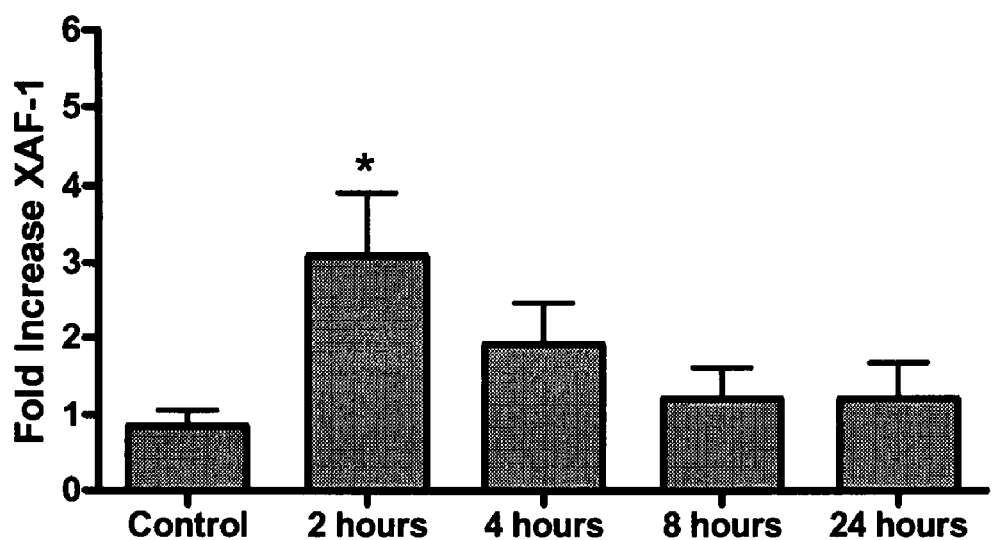
FIG. 4 is a graph illustrating that IFN-Beta (15000 U) significantly elevates XAF-1 mRNA in symptomatic EAE mice

As shown in FIG. 4, XAF-1 expression was significantly increased 2 hours post last injection relative to mice not receiving IFN-beta.

Discussion

We propose that the leading therapeutic for MS, interferon-β (IFN-β), alleviates the symptoms of this disease and prevents its progression by increasing production of XAF-1 that blocks the anti-apoptotic activity of the IAPs thereby facilitating the death of myelin-reactive immune cells and reducing inflammation in the brain. In MS patients who do not respond to IFN-β, there may be a failure of IFN-β to induce XAF-1 in autoreactive immune cells. Furthermore, aggressive forms of MS may be associated with lower levels of XAF-1 expression while higher expression levels of these genes may characterize benign forms of MS. XAF-1 gene expression patterns may form the basis of diagnostic tests predictive of MS disease category, symptom severity and IFN-β responsiveness. To utilize such tools for the prediction and treatment of human disease, the ultimate goal is to identify gene products that may serve as the basis for rapid, reliable and inexpensive protein-based blood tests for predicting responsiveness to IFN-β in MS patients. By being able to identify those patients that are most likely to benefit from IFN-β, it will be possible to better ensure the optimal use of resources allocated for this highly expensive treatment. This the observations described herein may be useful to produce new tools that would not only improve the clinical management of MS but also may serve as surrogate markers for biochemical efficacy of new MS therapeutics. Such assays would not only improve the clinical management of MS but may serve as surrogate markers for biochemical efficacy of new MS therapeutics. In parallel, these tests have the potential to enable significant cost savings in the context of minimizing treatments unlikely to offer therapeutic benefit and, in some cases, providing an alternative to costly MRI scans.

All publications mentioned in this specification are hereby incorporated by reference

OTHER EMBODIMENTS

While specific embodiments have been described, those skilled in the art will recognize many alterations that could be made within the spirit of the invention, which is defined solely according to the following claims:

We claim:

1. A method of determining interferon responsiveness in a patient suffering from quiescent secondary progressive MS or active secondary progressive MS, the method comprising:
   a) determining an amount of a XAF-1 gene expression level in a blood sample obtained from the patient, the patient being treated with the interferon; and
   b) correlating the amount of the XAF-1 gene expression level in the blood sample with the responsiveness of the patient to the interferon.

2. The method, according to claim 1, in which the XAF-1 gene expression level is compared to those of control subjects.

3. The method, according to claim 2, in which an increase in the XAF-1 gene expression level relative to those of the control subjects indicates that the patient is responsive to interferon therapy.

4. The method, according to claim 2, in which the control subjects are those having benign MS or are healthy normal subjects.

5. The method, according to claim 1, in which the XAF-1 gene expression level is determined by measuring the levels of transcribed XAF-1 mRNA in the blood sample.

6. The method, according to claim 5, in which the level of XAF-1 mRNA is measured using quantitative real time polymerase chain reaction (qRT-PCR).

7. The method, according to claim 1, in which the XAF-1 gene expression level is determined by measuring the level of XAF-1 protein in the blood sample.

8. The method, according to claim 7, in which the XAF-1 protein level is measured using an immunoassay.

9. The method, according to claim 1, in which the XAF-1 gene encodes XAF-1 protein.

10. The method, according to claim 1, in which peripheral blood mononuclear (PBMN) cells are isolated from the blood sample.

11. The method, according to claim 10, in which the XAF-1 gene expression level is measured in the PBMNs.

12. The method, according to claim 11, in the XAF-1 gene expression level is compared those of control subjects, an increase in the XAF-1 gene expression level relative to those of the control subjects indicates that the patient is responsive to interferon therapy.

13. The method, according to claim 12, in which the increased gene expression level includes increased levels of XAF-1 mRNA.

14. The method, according to claim 12, in which the control subjects are those having benign MS or are healthy normal subjects.

15. The method, according to claim 1, in which T cells are isolated from the blood sample.

16. The method, according to claim 15, in which the XAF-1 gene expression level is measured in the T cells.

17. The method, according to claim 16, in which the T cells are resting T cells.

18. The method, according to claim 16, in which the XAF-1 gene expression level is compared to those of control subjects, an increase in the XAF-1 gene expression level relative to those of the control subjects indicates that the patient is responsive to interferon therapy.

19. The method, according to claim 18, in which the increased gene expression level includes increased levels of XAF-1 mRNA.

20. The method, according to claim 18, in which the control subjects are those having benign MS or are healthy normal subjects.

21. The method, according to claim 1, in which the interferon is interferon-beta (IFN-β).

22. A method for determining a prognosis of a patient diagnosed with quiescent secondary progressive MS or active secondary progressive MS and undergoing IFN-β treatment, the method comprising: a) obtaining a blood sample from the patient; and b) determining whether the sample has an increased level of XAF-1 gene expression relative to that of a control subject, an increase in the level being an indication that the patient has a good prognosis and will respond to IFN-β therapy.

23. The method, according to claim 22, in which T cells or PBMNs are isolated from the blood sample.

24. The method, according to claim 23, in which XAF-1 gene expression levels are measured in the T cells or the PBMNs.

25. A method for monitoring the progress of IFN-β therapy in a patient suffering from quiescent secondary progressive MS or active secondary progressive MS, the method comprising: a) determining an amount of a XAF-1 gene expression level in a first blood sample obtained from the patient at first time period; b) determining an amount of the XAF-1 gene expression level in a second blood sample obtained from the patient at a second time period; and b) comparing in the XAF-1 gene expression levels, an increase in the XAF-1 gene expression level at the second time period being an indication that the patient is responding to the IFN-β therapy.

26. The method, according to claim 25, in which the XAF-1 gene expression level is determined by measuring the levels of transcribed XAF-1 mRNA in the blood sample.

27. The method, according to claim 26, in which the level of XAF-1 mRNA is measured using quantitative real time polymerase chain reaction (qRT-PCR).

28. The method, according to claim 25, in which the XAF-1 gene expression level is determined by measuring the level of XAF-1 protein in the blood sample.

29. The method, according to claim 28, in which the XAF-1 protein level is measured using an immunoassay.

30. The method, according to claim 25, in which the XAF-1 gene encodes XAF-1 protein.

31. The method, according to claim 25, in which peripheral blood mononuclear (PBMN) cells are isolated from the first and second blood samples.

32. The method, according to claim 31, in which the XAF-1 gene expression level is measured in the PBMNs.

33. The method, according to claim 25, in which T cells are isolated from the first and second blood samples.

34. The method, according to claim 33, in which the XAF-1 gene expression level is measured in the T cells.

35. The method, according to claim 34, in which the T cells are resting T cells.

36. A method of differentiating between quiescent secondary progressive multiple sclerosis and active secondary progressive multiple sclerosis in a patient undergoing IFN-β therapy, the method comprising: a) determining an amount of XAF-1 gene expression level in a blood sample obtained from the patient; and b) correlating the amount of the XAF-1 gene expression level in the blood sample with the presence of quiescent secondary progressive multiple sclerosis or active secondary progressive multiple sclerosis.

37. The method, according to claim 36, in which an increased level of the XAF-1 gene expression in T cells and PBMNs isolated from the patient blood sample being an indication that the patient is suffering from quiescent secondary progressive multiple sclerosis and not active secondary progressive multiple sclerosis.

* * * * *